(12) United States Patent
Deem et al.

(10) Patent No.: US 6,840,243 B2
(45) Date of Patent: Jan. 11, 2005

(54) METHODS AND DEVICES FOR USE IN PERFORMING PULMONARY PROCEDURES

(75) Inventors: Mark E. Deem, Mountain View, CA (US); Hanson S. Gifford, III, Woodside, CA (US); Ronald French, San Jose, CA (US); Douglas Sutton, Pacifica, CA (US)

(73) Assignee: Emphasys Medical, Inc., Redwood City, CA (US)

(*) Notice: Subject to any disclaimer, the term of this patent is extended or adjusted under 35 U.S.C. 154(b) by 82 days.

(21) Appl. No.: 10/419,508

(22) Filed: Apr. 18, 2003

(65) Prior Publication Data

US 2003/0192550 A1 Oct. 16, 2003

Related U.S. Application Data

(63) Continuation of application No. 09/519,735, filed on Mar. 4, 2000, now Pat. No. 6,679,264.

(51) Int. Cl.[7] .............................................. A61M 16/00
(52) U.S. Cl. ............................ 128/207.16; 128/200.26; 128/912
(58) Field of Search ..................... 128/200.26, 207.14, 128/207.15, 207.16, 912; 606/108; 623/9

(56) References Cited

U.S. PATENT DOCUMENTS

| | | | |
|---|---|---|---|
| 2,981,254 A | 4/1961 | Vanderbilt | 128/350 |
| 3,657,744 A | 4/1972 | Ersek | 128/334 |
| 3,788,327 A * | 1/1974 | Donowitz et al. | 604/247 |
| 3,874,388 A | 4/1975 | King et al. | 128/334 |
| 4,014,318 A | 3/1977 | Dockum et al. | 128/1 |
| 4,086,665 A | 5/1978 | Poirier | 623/1 |
| 4,212,463 A | 7/1980 | Repinski et al. | 273/418 |
| 4,250,873 A | 2/1981 | Bonnet | 600/104 |
| 4,302,854 A | 12/1981 | Runge | 3/1.7 |
| 4,477,930 A | 10/1984 | Totten et al. | 3/1.5 |

(List continued on next page.)

FOREIGN PATENT DOCUMENTS

| | | |
|---|---|---|
| EP | 0621 015 B1 | 10/1994 |
| EP | 0621 015 A1 | 10/1994 |
| EP | 1 078 601 A2 | 2/2001 |
| EP | 1 151 729 A1 | 11/2001 |
| GB | 2324729 | 4/1998 |
| RU | 2140211 | 10/1999 |
| SU | 852321 | 7/1981 |
| SU | 1371700 | 2/1988 |
| SU | 1593651 | 9/1990 |
| WO | 94/26175 | 11/1994 |

(List continued on next page.)

OTHER PUBLICATIONS

Al Jishi et al., "Selective Bronchial Occlusion for Treatment of Bullous Interstitial Emphysema and Bronchopleural Fistula." *J. of Pediatric Surgery*, 29:1545–1547, 1994.

(List continued on next page.)

Primary Examiner—Aaron J. Lewis
(74) Attorney, Agent, or Firm—Fish & Richardson P.C.; Fred C. Hernandez; Stephanie L. Seidman

(57) ABSTRACT

Systems, methods and devices for performing pulmonary procedures, and in particular treating lung disease. A flow control element includes a valve that prevents airflow in the inhalation direction but permits airflow in the exhalation direction. The flow control element is guided to and positioned at the site by a bronchoscope that is introduced into the patient's trachea and used to view the lungs during delivery of the flow control element. The valve may include one, two or more valve elements, and it may be collapsible for easier delivery. A source of vacuum or suction may be used to increase the amount of fluid withdrawn from the lung tissue. A device for measuring hollow structures, such as bronchioles, and a device for removing a previously-placed flow control element are disclosed as well.

48 Claims, 8 Drawing Sheets

U.S. PATENT DOCUMENTS

| | | | |
|---|---|---|---|
| 4,710,192 A | 12/1987 | Liotta et al. ................ 623/1 |
| 4,732,152 A | 3/1988 | Wallsten et al. ............ 128/343 |
| 4,759,758 A | 7/1988 | Gabbay ........................ 623/2 |
| 4,795,449 A | 1/1989 | Schneider et al. .......... 604/329 |
| 4,808,183 A | 2/1989 | Panje ............................ 623/9 |
| 4,819,664 A | 4/1989 | Nazari ................... 128/207.15 |
| 4,830,003 A | 5/1989 | Wolff et al. ................. 128/343 |
| 4,832,680 A | 5/1989 | Haber et al. ................. 600/31 |
| 4,846,836 A | 7/1989 | Reich ........................... 623/11 |
| 4,850,999 A | 7/1989 | Planck ........................... 623/1 |
| 4,852,568 A | 8/1989 | Kensey ...................... 128/325 |
| 4,877,025 A | 10/1989 | Hanson ................. 128/107.16 |
| 4,934,999 A | 6/1990 | Bader ........................... 600/29 |
| 4,968,294 A | 11/1990 | Salama ......................... 600/30 |
| 5,061,274 A | 10/1991 | Kensey ...................... 606/213 |
| 5,116,360 A | 5/1992 | Pinchuk et al. ................ 623/1 |
| 5,116,564 A | 5/1992 | Jansen et al. ................ 264/255 |
| 5,123,919 A | 6/1992 | Sauter et al. ................... 623/2 |
| 5,151,105 A | 9/1992 | Kwan-Gett .................... 623/1 |
| 5,158,548 A * | 10/1992 | Lau et al. .................... 606/194 |
| 5,161,524 A | 11/1992 | Evans ................... 128/203.15 |
| 5,306,234 A | 4/1994 | Johnson ........................ 604/49 |
| 5,352,240 A | 10/1994 | Ross ............................... 623/2 |
| 5,358,518 A | 10/1994 | Camilli .......................... 623/2 |
| 5,366,478 A | 11/1994 | Brinkerhoff et al. ........ 660/213 |
| 5,382,261 A | 1/1995 | Palmaz ....................... 606/158 |
| 5,392,775 A | 2/1995 | Adkins et al. .......... 128/207.16 |
| 5,409,019 A | 4/1995 | Wilk ........................... 128/898 |
| 5,411,507 A | 5/1995 | Heckele ...................... 606/108 |
| 5,411,552 A | 5/1995 | Andersen et al. .............. 623/2 |
| 5,413,599 A | 5/1995 | Imachi et al. .................. 623/2 |
| 5,417,226 A | 5/1995 | Juma ........................... 128/885 |
| 5,445,626 A | 8/1995 | Gigante ...................... 604/349 |
| 5,453,090 A | 9/1995 | Martinez et al. .............. 604/53 |
| 5,486,154 A | 1/1996 | Kelleher ..................... 600/104 |
| 5,499,995 A | 3/1996 | Teirstein .................... 606/192 |
| 5,500,014 A | 3/1996 | Quijano et al. ................. 623/2 |
| 5,562,608 A | 10/1996 | Sekins et al. ................. 604/20 |
| 5,645,519 A | 7/1997 | Lee et al. ................... 600/114 |
| 5,645,565 A | 7/1997 | Rudd et al. ................. 606/213 |
| 5,660,175 A | 8/1997 | Dayal ..................... 128/207.15 |
| 5,662,713 A | 9/1997 | Andersen et al. ............ 623/12 |
| 5,683,451 A | 11/1997 | Lenker et al. .................. 623/1 |
| 5,697,968 A | 12/1997 | Rogers et al. .................. 623/1 |
| 5,755,770 A | 5/1998 | Ravenscroft ................... 623/1 |
| 5,800,339 A | 9/1998 | Salama ......................... 600/29 |
| 5,803,080 A | 9/1998 | Freitag .................... 128/207.14 |
| 5,840,081 A | 11/1998 | Andersen et al. .............. 623/2 |
| 5,851,232 A | 12/1998 | Lois ................................ 623/1 |
| 5,855,587 A | 1/1999 | Hyon et al. ................. 606/188 |
| 5,855,597 A | 1/1999 | Jayaraman ..................... 623/1 |
| 5,855,601 A | 1/1999 | Bessler et al. .................. 623/2 |
| 5,944,738 A | 8/1999 | Amplatz et al. ............ 606/213 |
| 5,947,997 A | 9/1999 | Pavcnik et al. ............. 606/213 |
| 5,954,766 A * | 9/1999 | Zadno-Azizi et al. ....... 623/1.24 |
| 5,957,949 A | 9/1999 | Leonhardt et al. .......... 606/194 |
| 5,976,174 A | 11/1999 | Ruiz ........................... 606/213 |
| 5,980,455 A | 11/1999 | Daniel et al. ............... 600/235 |
| 5,984,965 A | 11/1999 | Knapp et al. ................. 623/12 |
| 6,007,575 A | 12/1999 | Samuels ........................ 623/1 |
| 6,009,614 A | 1/2000 | Morales ....................... 29/516 |
| 6,020,380 A | 2/2000 | Killian ....................... 514/570 |
| 6,022,312 A | 2/2000 | Chaussy et al. .............. 600/29 |
| 6,027,525 A | 2/2000 | Suh et al. ....................... 623/1 |
| 6,051,022 A | 4/2000 | Cai et al. ........................ 623/2 |
| 6,068,635 A | 5/2000 | Gianotti ..................... 606/108 |
| 6,068,638 A | 5/2000 | Makower ................... 606/159 |
| 6,077,291 A | 6/2000 | Das ............................ 606/213 |
| 6,083,255 A * | 7/2000 | Laufer et al. ................. 607/96 |
| 6,123,663 A | 9/2000 | Rebuffat |
| 6,135,729 A | 10/2000 | Aber ........................... 417/420 |
| 6,135,991 A | 10/2000 | Muni et al. ................. 604/509 |
| 6,141,855 A | 11/2000 | Morales ....................... 29/516 |
| 6,162,245 A | 12/2000 | Jayaraman ................. 623/1.15 |
| 6,168,614 B1 | 1/2001 | Andersen et al. .............. 623/1 |
| 6,174,323 B1 | 1/2001 | Biggs et al. ................. 606/232 |
| 6,183,520 B1 | 2/2001 | Pintauro et al. .......... 623/23.64 |
| 6,190,381 B1 | 2/2001 | Olsen et al. .................. 606/32 |
| 6,200,333 B1 | 3/2001 | Laufer .......................... 607/96 |
| 6,206,918 B1 | 3/2001 | Campbell et al. .......... 623/2.32 |
| 6,234,996 B1 | 5/2001 | Bagaoisan et al. ........ 604/97.01 |
| 6,240,615 B1 | 6/2001 | Kimes et al. ................. 29/516 |
| 6,245,102 B1 | 6/2001 | Jayaraman ................. 623/1.15 |
| 6,258,100 B1 | 7/2001 | Alferness et al. ........... 606/108 |
| 6,270,527 B1 | 8/2001 | Campbell et al. .......... 623/2.18 |
| 6,287,290 B1 | 9/2001 | Perkins et al. .............. 604/516 |
| 6,293,951 B1 * | 9/2001 | Alferness et al. ........... 606/108 |
| 6,302,893 B1 | 10/2001 | Limon et al. ............... 606/108 |
| 6,312,407 B1 | 11/2001 | Zadno-Azizi et al. .. 604/103.03 |
| 6,325,777 B1 | 12/2001 | Zadno-Azizi et al. .... 604/97.01 |
| 6,325,778 B1 | 12/2001 | Zadno-Azizi et al. .... 604/99.02 |
| 6,327,772 B1 | 12/2001 | Zadno-Azizi et al. ......... 29/557 |
| 6,328,689 B1 | 12/2001 | Gonzalez et al. ............. 600/37 |
| 6,355,014 B1 | 3/2002 | Zadno-Azizi et al. .... 604/99.02 |
| 6,398,775 B1 | 6/2002 | Perkins et al. .............. 604/514 |
| 6,402,754 B1 | 6/2002 | Gonzalez ...................... 606/69 |
| 6,416,554 B1 | 7/2002 | Alferness et al. ......... 623/23.65 |
| 6,458,076 B1 * | 10/2002 | Pruitt .......................... 600/146 |
| 6,485,407 B2 | 11/2002 | Alferness et al. ............. 600/37 |
| 6,491,706 B1 | 12/2002 | Alferness et al. ........... 606/157 |
| 6,493,589 B1 | 12/2002 | Medhkour et al. ............ 607/99 |
| 6,510,846 B1 | 1/2003 | O'Rourke .............. 128/200.21 |
| 6,527,761 B1 | 3/2003 | Buch et al. .................. 604/516 |
| 6,558,318 B1 | 5/2003 | Daniel et al. ............... 600/213 |
| 6,592,594 B2 | 7/2003 | Rimbaugh et al. .......... 606/108 |
| 6,679,264 B1 * | 1/2004 | Deem et al. ........... 128/207.16 |
| 6,694,979 B2 | 2/2004 | Hundertmark et al. . 128/207.14 |
| 6,699,231 B1 | 3/2004 | Sterman et al. ............. 604/509 |
| 2001/0025132 A1 | 9/2001 | Alferness et al. ............. 600/37 |
| 2001/0037808 A1 | 11/2001 | Deem et al. ........... 128/200.24 |
| 2001/0041906 A1 | 11/2001 | Gonzalez .................... 606/191 |
| 2001/0051799 A1 | 12/2001 | Ingenito ..................... 604/516 |
| 2001/0052344 A1 | 12/2001 | Doshi .......................... 128/207 |
| 2001/0056274 A1 | 12/2001 | Perkins et al. .............. 604/516 |
| 2002/0007831 A1 | 1/2002 | Davenport et al. .... 128/200.24 |
| 2002/0026233 A1 | 2/2002 | Shaknovich ............... 623/1.24 |
| 2002/0062120 A1 | 5/2002 | Perkins et al. .............. 604/516 |
| 2002/0077593 A1 | 6/2002 | Perkins et al. ........... 604/96.01 |
| 2002/0077696 A1 | 6/2002 | Zadno-Azizi et al. ...... 623/1.24 |
| 2002/0087153 A1 | 7/2002 | Roschak et al. .............. 606/27 |
| 2002/0095209 A1 | 7/2002 | Zadno-Azizi et al. ...... 623/1.24 |
| 2002/0111619 A1 | 8/2002 | Keast et al. ................... 606/41 |
| 2002/0111620 A1 | 8/2002 | Cooper et al. ................ 606/41 |
| 2002/0112729 A1 | 8/2002 | DeVore et al. .......... 128/207.15 |
| 2002/0138135 A1 | 9/2002 | Duerig et al. .............. 623/1.24 |
| 2003/0018327 A1 | 1/2003 | Truckai et al. ................ 606/32 |
| 2003/0018344 A1 | 1/2003 | Kaji et al. ................... 606/130 |
| 2003/0050648 A1 | 3/2003 | Alferness et al. ........... 606/108 |
| 2003/0070683 A1 | 4/2003 | Deem et al. ........... 128/207.16 |
| 2003/0075169 A1 | 4/2003 | Deem et al. ........... 128/200.19 |
| 2003/0075170 A1 | 4/2003 | Deem et al. ........... 128/200.19 |
| 2003/0083671 A1 | 5/2003 | Rimbaugh et al. .......... 606/108 |
| 2003/0192551 A1 | 10/2003 | Deem et al. ........... 128/207.14 |
| 2004/0016435 A1 | 1/2004 | Deem et al. ........... 128/207.14 |

FOREIGN PATENT DOCUMENTS

| | | |
|---|---|---|
| WO | 95/32018 | 11/1995 |
| WO | 96/34582 | 11/1996 |
| WO | 97/44085 | 11/1997 |
| WO | 98/00840 | 1/1998 |
| WO | 98/19633 | 5/1998 |

| WO | 98/39047 | 9/1998 |
| WO | 98/44854 A1 | 10/1998 |
| WO | 98/48706 | 11/1998 |
| WO | 99/01076 | 1/1999 |
| WO | 99/13801 | 3/1999 |
| WO | 99/26692 | 6/1999 |
| WO | 99/32040 | 7/1999 |
| WO | 99/42059 | 8/1999 |
| WO | 99/42161 | 8/1999 |
| WO | 99/64109 A1 | 12/1999 |
| WO | 00/15149 | 3/2000 |
| WO | 00/42950 | 7/2000 |
| WO | 00/51510 | 9/2000 |
| WO | 00/62699 | 10/2000 |
| WO | 00/78386 A1 | 12/2000 |
| WO | 00/78407 A1 | 12/2000 |
| WO | 01/02042 A1 | 1/2001 |
| WO | 01/03642 A1 | 1/2001 |
| WO | 01/05334 A1 | 1/2001 |
| WO | 01/10313 A1 | 2/2001 |
| WO | 01/10314 A2 | 2/2001 |
| WO | 01/12104 A1 | 2/2001 |
| WO | 01/13839 A1 | 3/2001 |
| WO | 01/13908 A2 | 3/2001 |
| WO | 01/28433 A1 | 4/2001 |
| WO | 01/45590 A2 | 6/2001 |
| WO | 01/49213 A2 | 7/2001 |
| WO | 01/54585 A1 | 8/2001 |
| WO | 01/54625 A1 | 8/2001 |
| WO | 01/54685 A1 | 8/2001 |
| WO | 01/66190 A2 | 9/2001 |
| WO | 01/74271 A1 | 10/2001 |
| WO | 01/87170 A1 | 11/2001 |
| WO | 01/89366 A2 | 11/2001 |
| WO | 01/95786 A2 | 12/2001 |
| WO | 02/05884 A2 | 1/2002 |
| WO | 02/22072 A2 | 3/2002 |
| WO | 02/32333 A1 | 4/2002 |
| WO | 02/34322 A2 | 5/2002 |
| WO | 02/38038 A2 | 5/2002 |
| WO | 02/47575 A2 | 6/2002 |
| WO | 02/056794 A2 | 7/2002 |
| WO | 02/064045 A1 | 8/2002 |
| WO | 02/064190 A3 | 8/2002 |
| WO | 02/064190 A2 | 8/2002 |
| WO | 02/069823 A3 | 9/2002 |
| WO | 02/069823 A2 | 9/2002 |
| WO | 02/094087 A1 | 11/2002 |
| WO | 03/022124 A2 | 3/2003 |

OTHER PUBLICATIONS

Article: "Autocath® 100—Nonsurgical, Intraurethral Bladder Control Device for Incontinent and Retentive Women—Dr. Kulisz's Development".

Derwent citing Russian Patent No. RU 2140211, published Oct. 27, 1999, for: "Method of surgical treatment of patients with pathology of respiratory organs complicated with pulmonary hemorrhages".

Derwent citing Soviet Union Patent No. SU 852–321, published Jul. 8, 1981, for: "Treatment for acute pulmonary and pleural disease in children—by pneumo–abcessotomy simultaneous with occlusion of affected lung part".

Derwent# 007607249 WPI Acc. No: 1988–241181/198834 (citing Russian Application No. SU4026409, published Feb. 21, 1986), Russian Patent No. SU 1371700.

Derwent# 008650867 WPI Acc. No: 1991–154896/199121 (citing Russian Application No. SU4280143, published Jul. 7, 1987), Russian Patent No. SU 1593651.

Harris et al., "The Experimental Production in Dogs of Emphysema with Associated Asthmatic Syndrome by Means of an Intratracheal Ball Valve", *J. Lab. Clini. Med.*, 9(iv):75–88, 1919.

Lewis et al., "Pulmonary Interstitial Emphysema: Selective Broncial Occlusion with a Swan–Ganz Catheter", *Archives of Disease in Childhood*, 63:313–315, 1988.

Mathew et al., "Selective bronchial obstruction for treatment of bullous interstitial emphysema." *J. of Ped.*, 96:475–477, 1980.

Okada et al., "Emergent Bronchofiberoptic Bronchial Occlusion for Intractable Pneumothorax with Severe Emphysema", *The Jap. J. of Thor. And Cardio. Sur.*, 46:1078–1081, 1998.

Puhakka et al., "Acute Bronchial Obstruction: An Experimental Rabbit Model Study", *Int. J. of Pediatric Otorhinolaryngology*, 18:107–118, 1989.

Snider et al., *The Definition of Emphysema*: Report of the National Heart Lung and Blood Institute, Division of Lung Diseases Workshop, *Am. Rev. Respir. Dis.*, 132:182–185, 1985.

Woodring et al., "Pneumothorax ex Vacuo", *Chest*, 100:1102–1124, 1996.

* cited by examiner

METHODS AND DEVICES FOR USE IN PERFORMING PULMONARY PROCEDURES

CROSS-REFERENCE TO RELATED APPLICATION

This application is a continuation of U.S. patent application Ser. No. 09/519,735 filed Mar. 4, 2000 now U.S. Pat. No. 6,679,264 entitled "Methods and Devices for use in Performing Pulmonary Procedures" by Deem et al., the full disclosure of which is incorporated herein by reference.

BACKGROUND OF THE INVENTION

1. Field of the Invention

The present invention relates generally to methods and devices for use in performing pulmonary procedures, and more particularly, procedures for treating various diseases of the lungs.

2. Description of Related Art

Pulmonary diseases such as emphysema and chronic obstructive pulmonary disease (COPD) reduce the ability of one or both lungs to fully expel air during the exhalation phase of the breathing cycle. The diseased lung tissue is less elastic than healthy lung tissue, which is one factor that prevents full exhalation of air. During breathing, the diseased portion of the lung does not fully recoil due to the tissue being less elastic. Consequently, the diseased (e.g., emphysematic) lung tissue exerts a relatively low driving force, which results in the diseased lung expelling less air volume than a healthy lung. The reduced air volume exerts less force on the airway which allows the airway to close before all air has been expelled, another factor that prevents full exhalation.

The problem is further compounded by the diseased, less elastic tissue that surrounds the very narrow airways that lead to the alveoli (the air sacs where oxygen-carbon dioxide exchange occurs). This tissue has less tone than healthy tissue and is typically unable to maintain the narrow airways open until the end of the exhalation cycle. This traps air in the lungs and exacerbates the already-inefficient breathing cycle. The trapped air causes the tissue to become hyper-expanded and no longer able to effect efficient oxygen-carbon dioxide exchange. Applying suction to these narrow airways (a procedure proposed in the literature for deflating the diseased portion of the lung) may collapse the airways due to the surrounding diseased tissue, thereby preventing successful fluid removal.

In addition, hyper-expanded lung tissue occupies more of the pleural space than healthy lung tissue. In most cases, a portion of the lung is diseased while the remaining part is healthy and therefore still able to efficiently carry out oxygen exchange. By taking up more of the pleural space, the hyper-expanded lung tissue reduces the amount of space available to accommodate the healthy, functioning lung tissue. As a result, the hyper-expanded lung tissue causes inefficient breathing due to its own reduced functionality and because it adversely affects the functionality of adjacent healthy tissue.

Lung reduction surgery is a conventional method of treating lung diseases such as emphysema. A diseased portion of the lung is surgically removed which makes more of the pleural space available to accommodate the functioning, healthy portions of the lung. The lung is typically accessed through a median sternotomy or small lateral thoracotomy. A portion of the lung, typically the upper lobe of each lung, is freed from the chest wall and then resected, e.g., by a stapler lined with bovine pericardium to reinforce the lung tissue adjacent the cut line and also to prevent air or blood leakage. The chest is then closed and tubes are inserted to remove air and fluid from the pleural cavity. The conventional surgical approach is relatively traumatic and invasive, and, like most surgical procedures, is not a viable option for all patients.

More recently proposed treatments include the use of devices that employ RF or laser energy to cut, shrink or fuse diseased lung tissue. Another lung volume reduction device utilizes a mechanical structure that is used to roll the lung tissue into a deflated, lower profile mass that is permanently maintained in a compressed condition. As for the type of procedure used, open surgical, minimally invasive and endo-bronchial approaches have all been proposed. Another proposed device (disclosed in publication no. WO 98/48706) is positioned at a location in the lung to block airflow and isolate a part of the lung. The publication states that the occlusion device is introduced through an endobronchial delivery device, and is resiliently deformable in order to provide a complete seal against airflow.

The search for new and better treatments underscores the drawbacks associated with existing pulmonary procedures. Accordingly, there is a need in the art for improved methods and devices for performing pulmonary procedures, and in particular, treating lung diseases such as emphysema.

SUMMARY OF THE INVENTION

In one embodiment the invention provides a method for treating a patient's lung. The method includes steps of selecting a hollow structure in a patient's lung, the hollow structure defining a pathway for conducting fluid flow in at least first and second directions, and allowing fluid flow within the pathway in the first direction while controlling fluid flow in the second direction.

In another embodiment the invention provides a method for treating a patient's lung. This method includes steps of providing a valve which allows fluid flow in a first direction and limits fluid flow in a second direction, and positioning the valve at a desired location in a lung of a patient with the first direction corresponding to an exhalation direction and the second direction corresponding to an inhalation direction.

In another embodiment the invention provides a method for treating a patient's lung that includes steps of providing a flow control element that limits fluid flow in at least one direction, positioning the flow control element at a location in a lung of a patient with the one direction substantially corresponding to an inhalation direction, and removing the flow control element after a period of time.

In another embodiment the invention provides a method for treating a patient's lung, the method comprising steps of selecting a hollow structure in a patient's lung, the hollow structure defining a pathway for conducting fluid flow in at least first and second directions, applying suction to draw fluid through the pathway in the first direction, and substantially preventing fluid flow through the pathway in the second direction.

In another embodiment the invention provides a system for treating a patient's lung. The system includes a flow control element sized and configured to be positioned in a hollow structure located in a patient's lung, the flow control element including a valve member that permits fluid flow in a first direction while substantially preventing fluid flow in a second direction. A delivery device is sized and configured to be guided to and positioned in or adjacent the hollow structure, and the flow control element is removably mounted on the delivery device.

In another embodiment the invention provides a system for treating a patient's lung. The system includes a measuring device for determining the approximate size of a hollow structure in a patient's lung, and a flow control element sized and configured to be positioned in a hollow structure located in a patient's lung, wherein the flow control element allows fluid flow in a first direction but substantially prevents fluid flow in a second direction.

In another embodiment the invention provides a system for treating a patient's lung. This system includes a flow control element sized and configured to be positioned in a hollow structure located in a patient's lung, wherein the flow control element allows fluid flow in a first direction but substantially prevents fluid flow in a second direction, and a removal device for removing the flow control element from the hollow structure subsequent to positioning the flow control element in the hollow structure.

DETAILED DESCRIPTION OF PREFERRED EMBODIMENTS

The present invention provides methods and devices for performing pulmonary procedures, for example, treating various lung diseases such as emphysema and COPD. One preferred embodiment of the invention provides a flow control element that allows fluid flow in a first direction and controls fluid flow in a second direction. As used herein, fluid means gas, liquid, or a combination of a gas(es) and liquid(s). In addition, controlled fluid flow, as used herein, means that the flow is altered in some manner, i.e., the flow is not unimpeded in the second direction. The specific manner in which fluid flow is controlled in the second direction depends on the construction of the flow control element. The flow control element may, for example, completely block, substantially block, limit, meter or regulate fluid flow in the second direction by a valve or other suitable structure.

As an example, when positioned in a hollow structure in a patient's body, such as a bronchiole in one of the lungs, the flow control element is oriented to allow flow in the exhalation direction but prevent fluid flow in the inhalation direction. The flow control element has a valve member that opens during exhalation in order to deflate or decompress the isolated lung portion distal to the flow control element. This maintains the diseased tissue in a decompressed state which prevents further hyper-expansion of the tissue. The invention also permits slow decompression of the lung tissue over a short or extended period of time.

The invention thus may be used to prevent fluid being drawn into one ore more portions of a patient's lung. According to another aspect of the invention, a portion of the lung may be deflated by applying gentle suction (via the flow control element) to the hyper-expanded tissue without collapsing the walls of the narrow airways surrounded by diseased tissue. The suction draws air, liquid, mucous, etc., out of the lung portion to evacuate the diseased tissue. It will be recognized that these and other aspects of the invention may be practiced independently or in conjunction with each other.

Figure 1:
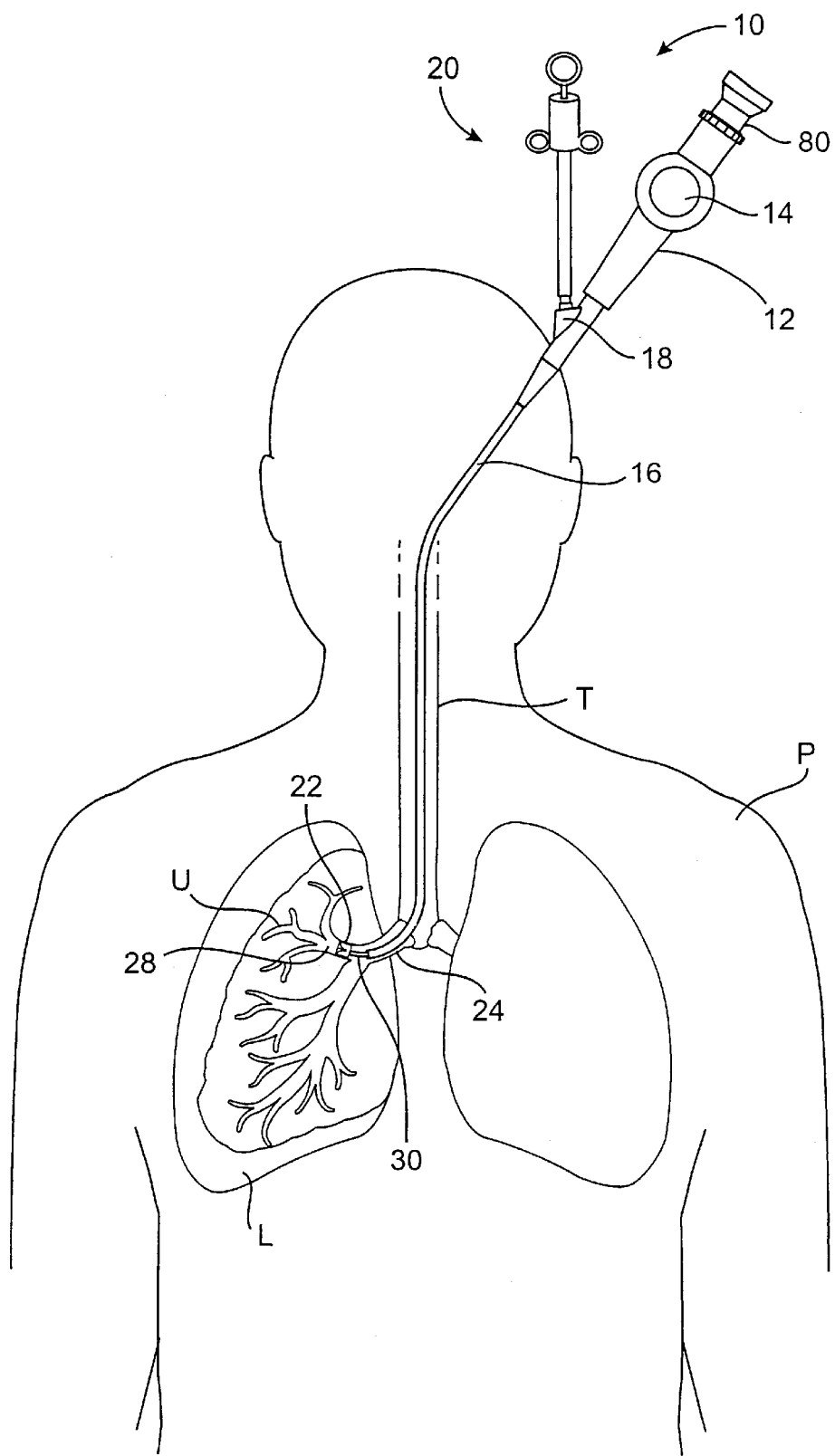
FIG. 1 is an elevation view schematically showing a system constructed according to one embodiment of the invention, the system being used to perform a pulmonary procedure on a patient.

FIG. 1 is a schematic view showing a system 10 constructed according to one embodiment of the invention for carrying out a pulmonary procedure on the lung L of a patient P. It should initially be noted that suitable systems, methods or devices outside of those specifically described herein may be used to practice the invention. As such, the system 10 is exemplary only and includes a bronchoscope 12 having a steering mechanism schematically indicated at 14, a shaft 16, and a port 18 which provides access to one or more working channels of the bronchoscope.

FIG. 1 shows a delivery device 20 constructed according to the invention. The delivery device 20 is shown positioned in the bronchoscope 12 in order to deliver a flow control element 22. The bronchoscope 12 has been passed into the patient's trachea T and guided into the right bronchus 24. The delivery device 20 is then manipulated with respect to the bronchoscope 12 via steering mechanism 14 to control placement of the flow control element 22. With reference to FIGS. 1 and 7–9, the delivery device 20 is movable within a bronchoscope working channel 26 (FIG. 8) and is guided into the desired location in the hollow structure, which in this case is a bronchiole 28. For purposes of explanation, the bronchiole 28 feeds an upper lobe U of the lung L which represents a diseased lung portion. The delivery device 20 is placed through the side port 18 and into the working channel 26, the distal end 30 of the delivery device 20 is moved out of the working channel, and the flow control element 22 is secured in position in the bronchiole 28.

Figure 2:
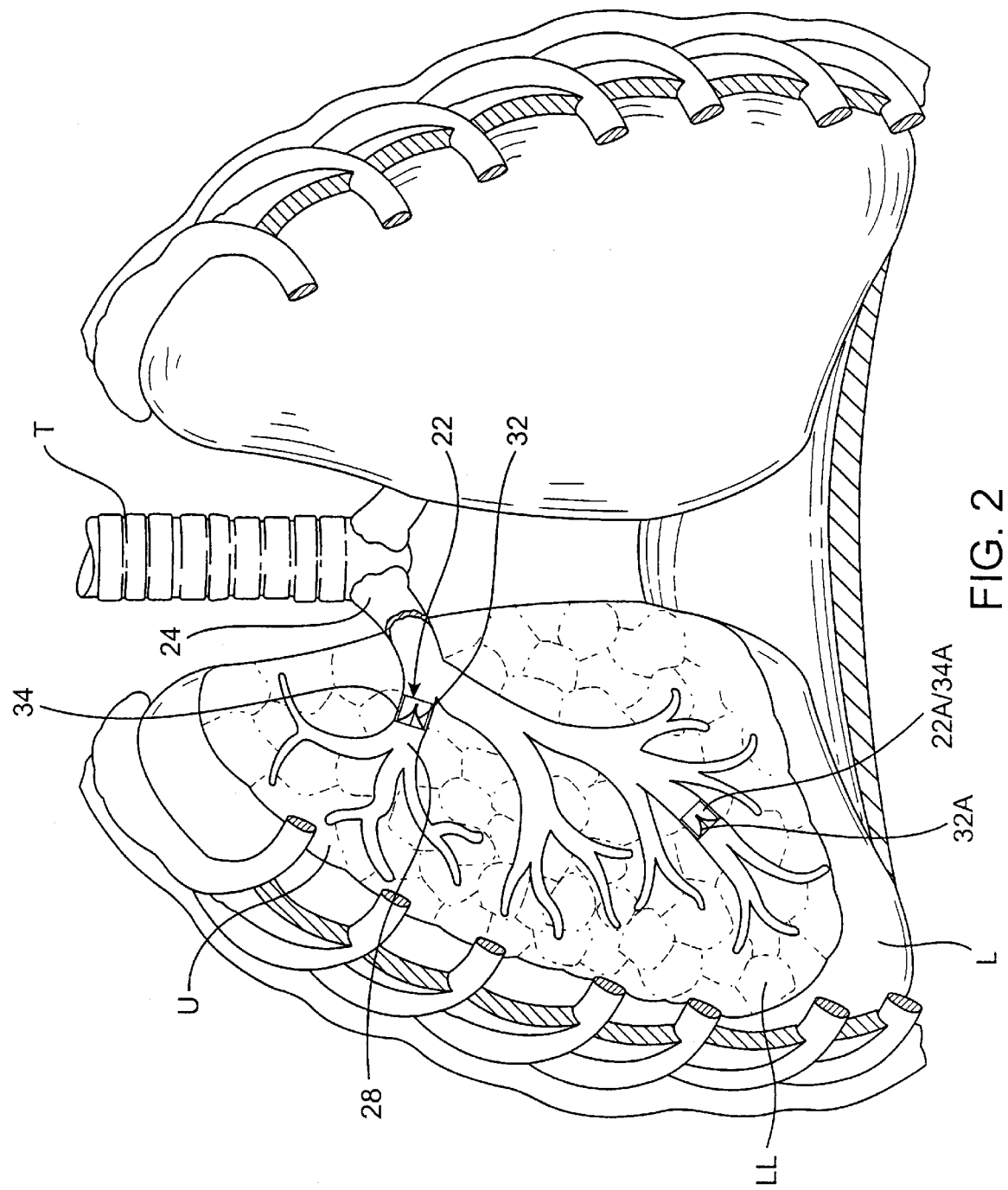
FIG. 2 is an enlarged elevation view of the lungs of the patient shown in FIG. 1 along with the system of the invention.
Figures 3, 4:
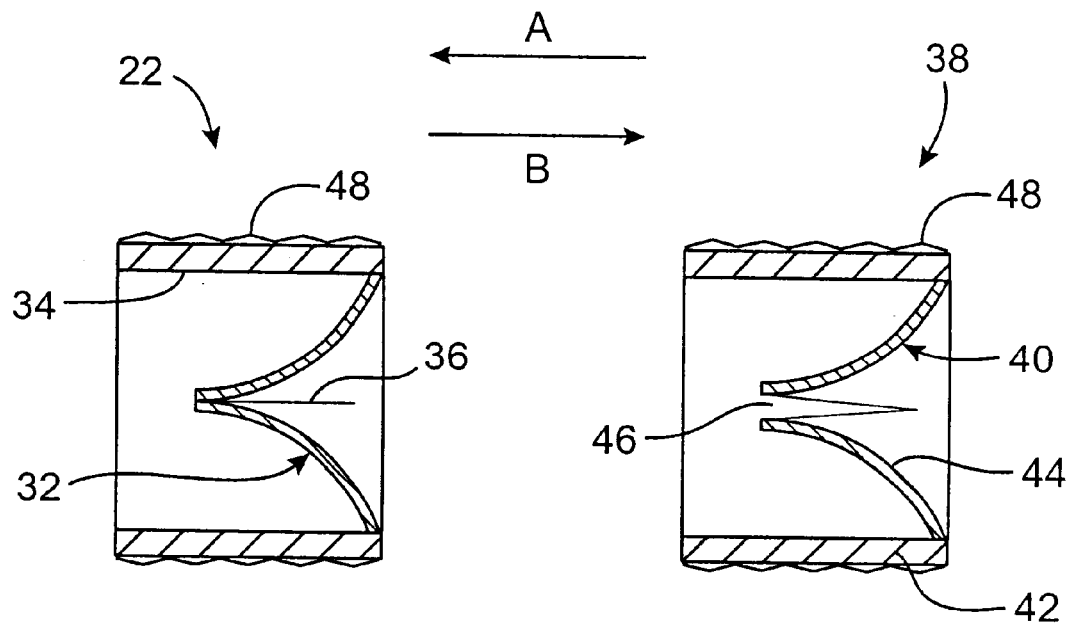
FIG. 3 is an enlarged elevation view, in section, of a flow control element forming part of the system shown in FIG. 2, wherein the flow control element allows fluid flow in a first direction but blocks fluid flow in a second direction.
FIG. 4 is an enlarged elevation view, in section, of an alternative flow control element that allows fluid flow in a first direction but blocks fluid flow in a second direction.

FIG. 2 is an enlarged view of the patient's lungs L shown in FIG. 1 after the introducer 12 and delivery device 20 have been removed, the flow control element 22 being left in the bronchiole 28. The flow control element 22, shown in more detail in FIG. 3, is in the form of a valve with a valve member 32 supported by a ring 34. It should be noted that FIG. 2 also illustrates a second flow control element 22A placed in a bronchiole 28A that feeds a lower lobe LL of the lung. The flow control element 22A includes a valve member 32A and a support ring 34A and reduces or prevents fluid from being inhaled into the hyper-expanded tissue of the lower lobe LL. It will be understood that any number of flow control elements may be used in a given procedure.

Referring to FIG. 3, which shows the flow control element 22 in detail, the valve member 32 is a duckbill-type valve and has two flaps defining an opening 36. The valve member 32 is shown in a flow-preventing orientation in FIG. 3 with the opening 36 closed. The valve member 32 is configured to allow fluid flow in a first direction (along arrow A) while controlling fluid flow in a second direction (along arrow B). In this embodiment, fluid flow in the direction of arrow B is controlled by being completely blocked by valve member 32. The first and second directions in which fluid flow is allowed and controlled, respectively, are preferably opposite or substantially opposite each other, for example, as shown in the Figures. It will be appreciated, though, that the invention may be practiced with the first and second directions different but not opposite each other.

As noted above, the valve member 32 of the flow control element 22 controls fluid flow by completely blocking such flow in the second direction. As such, the valve member 32 effectively functions as a one-way valve. Alternative embodiments of the invention utilize flow control elements that controls fluid flow in the second direction without completely blocking such flow.

FIG. 4 shows an exemplary flow control element 38 constructed according to an alternative embodiment of the invention that limits, but does not block, fluid flow in at least one direction. The flow control element 38 comprises a valve member 40 supported by a ring 42. The valve member 40 is preferably a duckbill-type valve having a similar construction to that of the valve member 32, except that the flaps 44 are formed, secured, oriented or otherwise configured to maintain a flow opening 46 when in their flow-controlling (as opposed to flow-allowing) orientation. The opening 46 is sized and configured to achieve desired flow characteristics through the flow control element 38.

When the flow control element 38 is in its flow-allowing orientation (not shown), the flaps 44 spread apart and allow essentially unimpeded fluid flow out of the diseased lung portion. When the flow control element 38 is in its flow-controlling orientation, as shown in FIG. 4, the flaps move together to define opening 46 which allows a predetermined amount of fluid to be inhaled into the lung portion. This is in contrast to flow control element 22 which blocks fluid flow into the lung when in a flow-controlling orientation. It will of course be recognized that FIG. 4 shows only one way to achieve limited fluid flow in a given direction. The specific manner in which flow control is obtained may vary according to the invention, e.g., by varying the number, size, shape or position of the flow openings on the flow control element.

Figure 5:
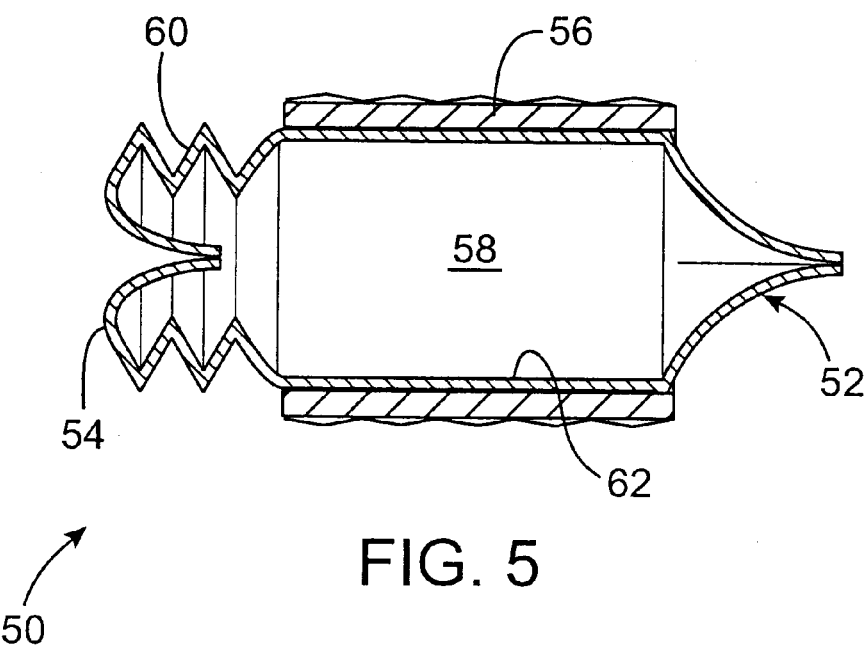
FIG. 5 is an enlarged elevation view, in section, of another alternative flow control element.

According to another aspect of the invention, the flow control element may be constructed to provide a pumping action that aids in moving gas or liquid within a hollow structure, such as a bronchiole. For instance, when the lung distorts during inhalation and/or exhalation, a mechanical pumping action is produced that may be used to move the gas or liquid to further deflate the isolated region of the lung. FIG. 5 shows an exemplary flow control element 50 constructed according to this embodiment and including a pair of valve members 52, 54 supported in series by a ring 56.

The valve members 52, 54 each include a pair of flaps defining a valve opening (the valve members being shown in their closed, fluid flow blocking orientation in FIG. 5). A chamber 58 is defined between the valve members 52, 54 and produces a pumping effect on the fluid flowing through the flow control element 50. The chamber would collapse and expand with movement of the bronchiole (or other hollow structure in which it is inserted) to pump fluid from the diseased lung tissue.

The valve member 54 is coupled to a bellows 60 to enhance the pumping action and/or to control the amount of force needed to open the valve member. The wall 62 defining the chamber 58 is secured to the ring 56 so that the chamber 58 occupies the entire interior of the ring 56. The flow control element 50 may have a different configuration wherein the chamber 58 is defined by an air pocket located within the wall 62. This may prevent fluid collecting in the chamber 58. In addition, a power-driven pump may be used to draw fluid out of the lungs, e.g., a miniature battery-powered electric pump, or pumps that use physical or chemical characteristics, e.g., a change in air temperature, presence of an additional gas or liquid, change in pH, etc., to generate pumping force that evacuates air and mucous.

Figure 6:
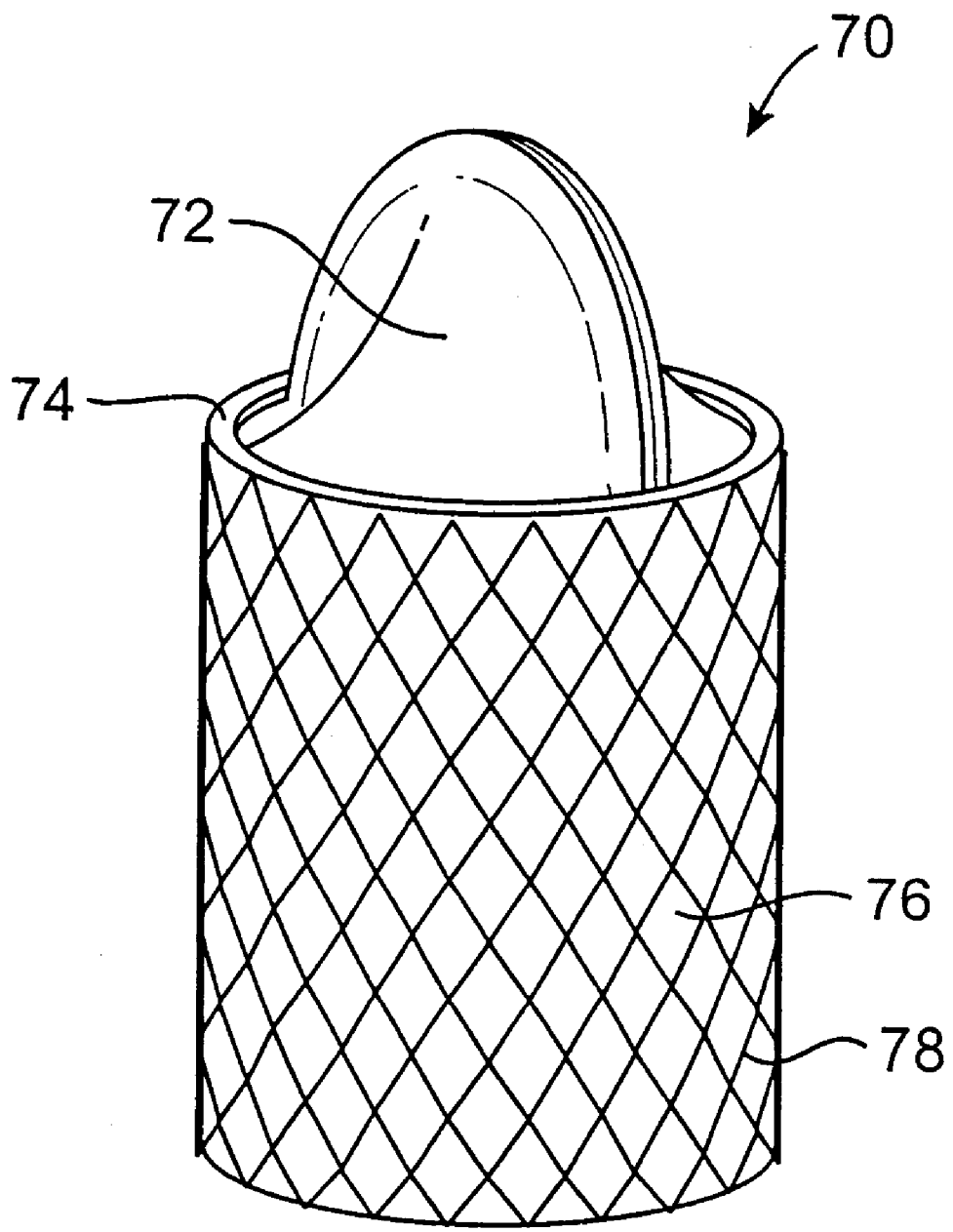
FIG. 6 is an enlarged elevation view, in section, of still another alternative flow control element.

FIG. 6 shows yet another alternative flow control element 70 including a valve member 72 comprising a pair of flaps defining an opening, and ring 74 supporting the valve member 72. The valve member 72 is a duckbill-type valve that permits fluid flow in a first direction but prevents flow in a second direction. The ring 74 in this embodiment comprises a stent 76 having struts 78 to enhance fixation of the flow control element 70 in the hollow body structure (not shown). The valve member 72 may be attached to the stent 76 by any suitable means, e.g., suture, fasteners, adhesives, etc. The stent 76 is movable between collapsed and expanded (FIG. 6) orientations to enable easy delivery and deployment. That is, the flow control element 70 including stent 76 may be collapsed and held in a sheath for delivery through a relatively small space, for example, the working channel of a bronchoscope. (A typical bronchoscope has a diameter of about 6 or 7 mm, while the working channel has a diameter of about 2 or 3 mm.) Utilizing a collapsible flow control element may also be useful in introducing the flow control element through an small opening formed in the patient's thorax.

Figure 7:
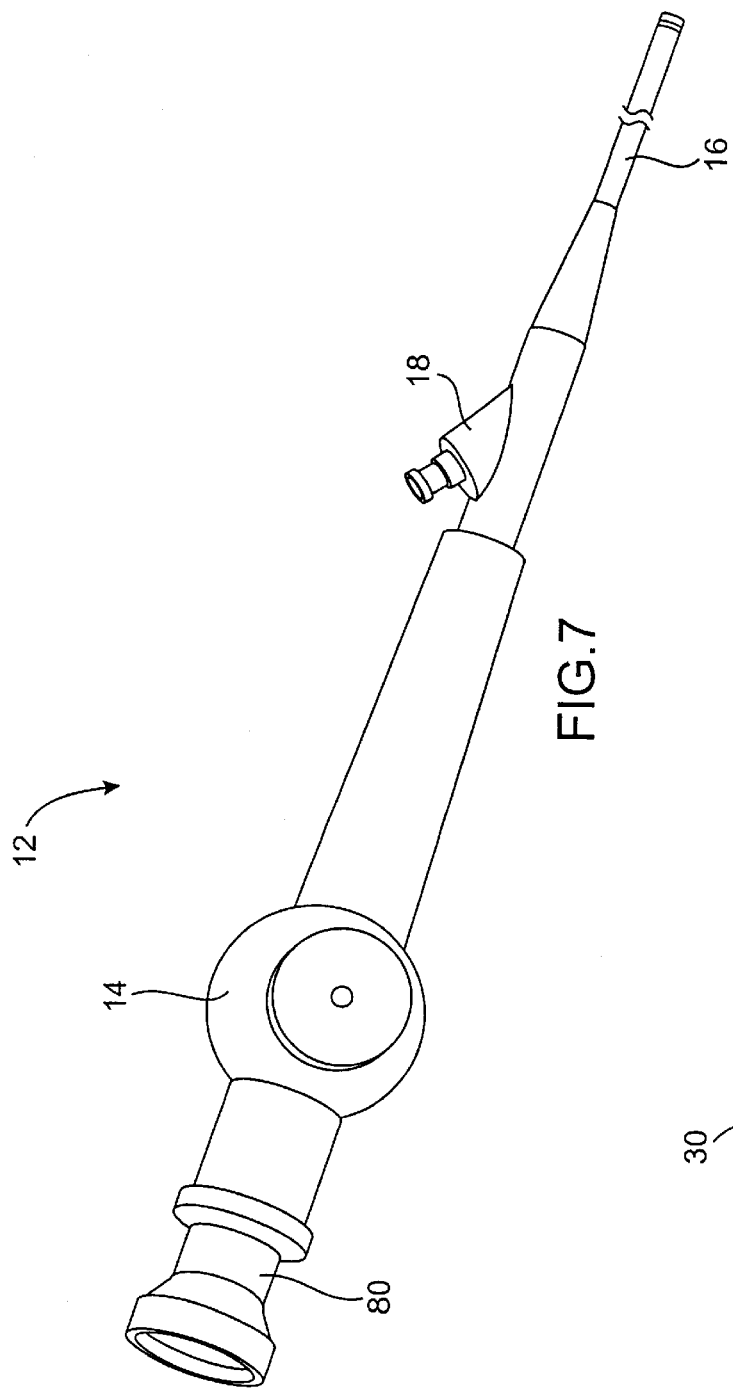
FIG. 7 is a perspective view of an introducer constructed according to another embodiment of the invention.
Figure 8:
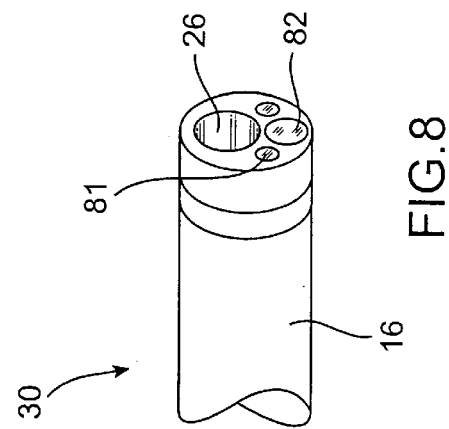
FIG. 8 is an enlarged perspective view of a portion of the introducer shown in FIG. 7.

FIGS. 7 and 8 show in detail the bronchoscope 12 and the flow control element delivery device 20 described above in connection with FIG. 1. The bronchoscope 12 has an eyepiece 80 which is used to visualize the trachea and the various pathways of the lung during deployment of the flow control element 22. The bronchoscope 12 may be provided with a camera/recorder, an aspiration/irrigation system, or other auxiliary features. The steering mechanism 14 may comprise cables that move the distal tip of the bronchoscope shaft 16 over a desired angular range, for example, 0° through 180°. FIG. 8 shows the distal portion 30 of the bronchoscope 12 including the working channel 26 (which communicates with the side port 18), one or more fiber optic light guides 81, and a lens 82 for transmitting images to the eyepiece 80.

Figure 9:
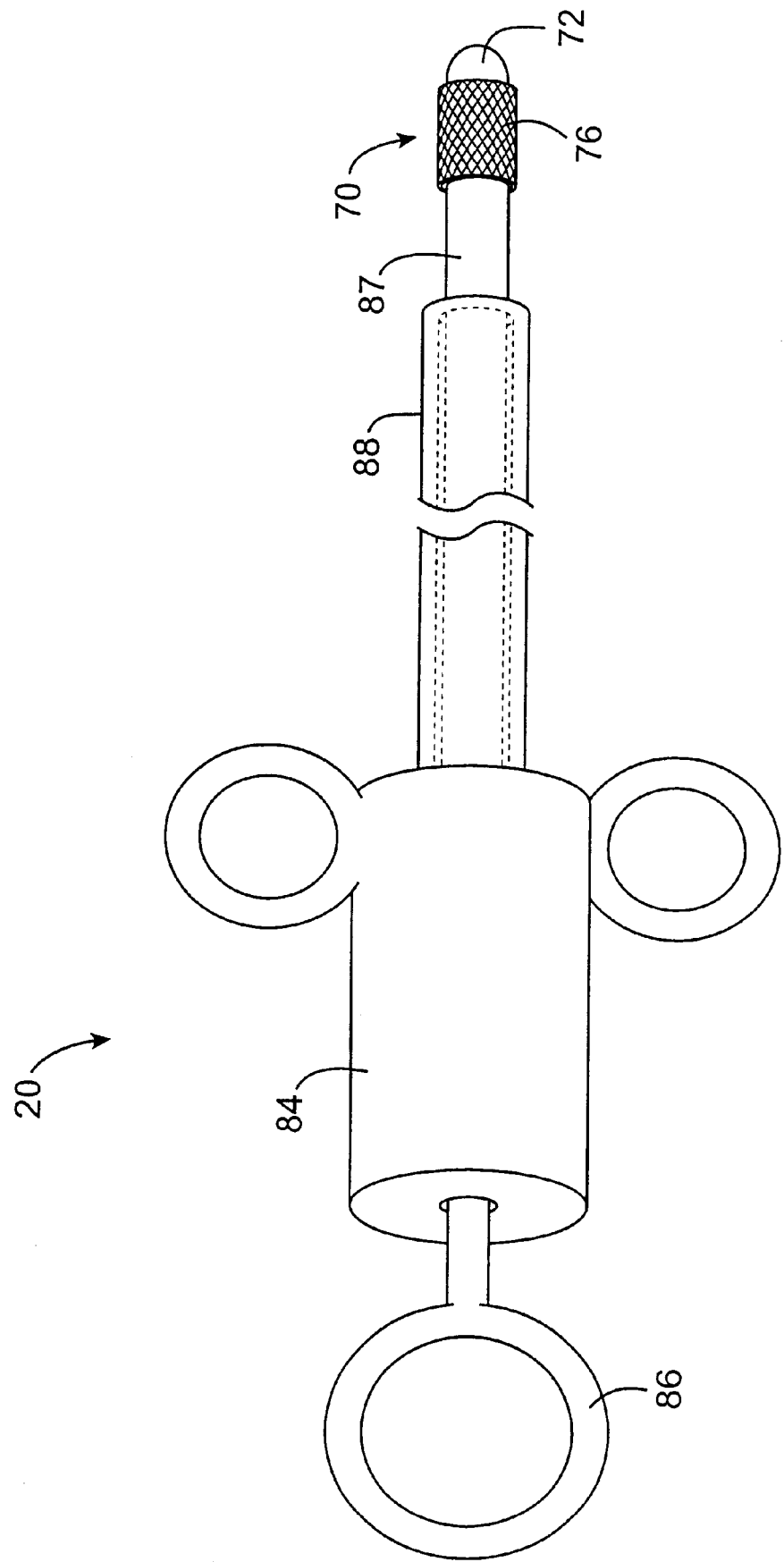
FIG. 9 is a perspective view of a delivery device constructed according to another embodiment of the invention for delivering a flow control element to a selected location in a patient's lung.

FIG. 9 shows the delivery device 20 to include a handle 84, an actuator 86, a support shaft 87 and a sheath 88. For purposes of illustration, the delivery device 20 will be described in connection with delivering the flow control element 70 of FIG. 6, although it will be understood that it may be used to deliver alternative flow control elements. The flow control element 70, and in particular the stent 76, is collapsed to a low profile orientation and then mounted on the shaft 87. The sheath 88 is moved distally from the position shown in FIG. 9 until it covers the stent body 76 (and the valve member 72, if desired) to maintain the flow control element 70 collapsed. (This position of the sheath is omitted for clarity.) The shaft 87 and sheath 88 are then passed into the side port 18 and working channel 26 of the bronchoscope 12 and guided to a desired location in the lung. The actuator 86 is used to remove the sheath 88 from the flow control element 70 which allows the stent 76 to expand. Stent 76 is preferably formed of a self-expanding material, e.g., nitinol. In this case the flow control element 70 immediately expands and engages the tissue upon retraction of sheath 88. Alternatively, the stents could rely on a mechanism such as a balloon or heat activation to expand in use.

The flow control element of the invention may be guided to and positioned at a desired location in the pulmonary system, such as the bronchiole 28 shown in FIGS. 1 and 2, by various delivery devices or systems. For example, guidewire-based systems, introducer sheaths, cannulae or catheters, etc., may be used to deliver the treatment element in a minimally invasive manner. The above-described method for using a bronchoscope to introduce the flow control element may be modified by placing an introducer sheath over the bronchoscope. The sheath provides access should the bronchoscope need to be removed from patient's body, for example, in order to place a different size flow control element.

Figure 10:
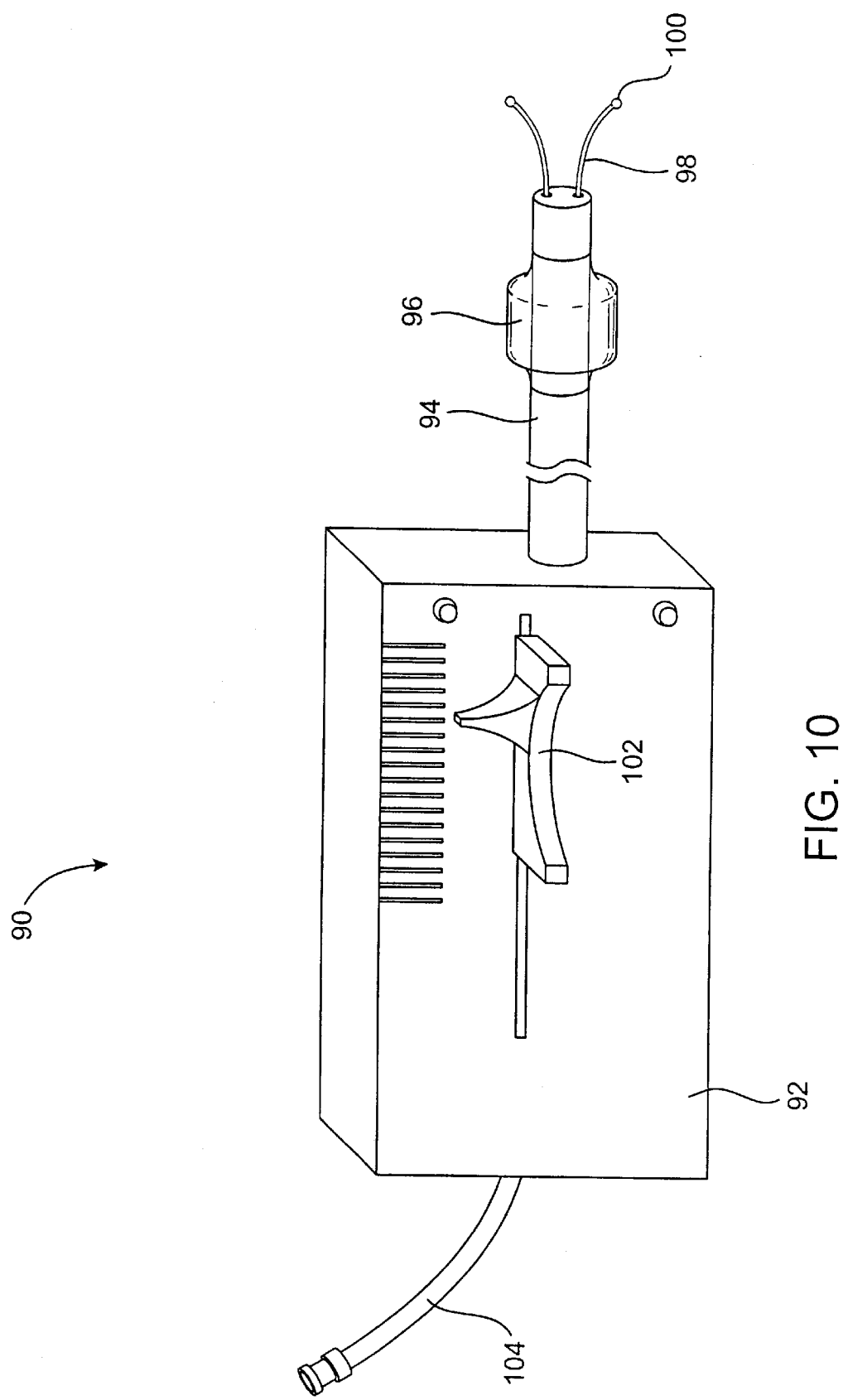
FIG. 10 is a perspective view of a measuring device constructed according to another embodiment of the invention for determining the size of a hollow structure prior to disposing a flow control element in the structure.

The invention is preferably carried out by first determining the approximate size of the target lumen, i.e., the hollow structure in which the flow control element will be placed. FIG. 10 shows somewhat schematically an exemplary device for determining the size of a hollow structure in a patient's body, for example, a bronchiole in a lung. The device 90 includes a housing 92, shaft 94, positioning element, 96 and measuring elements 98. The measuring elements 98 have tips 100 that are moved into contact with the wall of the hollow structure, such as the inner surface of a bronchiole (not shown). The device 90 is calibrated so that when tips 100 of measuring elements 98 engage the wall of the bronchiole the indicator 102 displays the approximate size of the bronchiole. An electrical coupling 104 powers the device 90.

The positioning element 96 is optional and may be used to fix the position of the measuring elements 98 within the bronchiole so as to obtain more precise measurement. The illustrated element 96 is an inflatable balloon, although other elements could be used to center and hold the shaft 96 within the bronchiole. Any suitable means may be used for ensuring that the measuring elements 98 do in fact contact the bronchiole wall in order to provide a true reading. The measuring elements 98 may be moved distally (to the right in FIG. 10) until a visual indicator indicates that the tips 100 are in contact with tissue. Alternatively, a change in electrical resistance may be used to confirm contact between the measuring elements 98 and tissue. It should be noted that the device 90 is merely representative of the various means that may be used to determine the size of a hollow body structure.

In use, the shaft 94 of the measuring device 90 is passed through the bronchoscope working channel 26 and delivered to the site. The device 90 is then operated as described above to determine the approximate size of the bronchiole. The degree of precision with which the size of the hollow structure is measured will depend on the procedure being performed and user preference. After determining the size of the bronchiole the device 90 is removed from working channel 26, and delivery device 20 is inserted into the channel to deploy the flow control element in the bronchiole.

It may in some instances be necessary or desirable to remove a flow control element from a hollow structure in which it has been deployed. As an example, it may be the case that placement of a flow control element for a given period of time effects beneficial results on the diseased lung tissue. The time during which the diseased tissue is deflated and decompressed may allow the tissue to regain some elasticity as a result of being temporarily inactive. After the tissue has regained some or all of its elasticity, it would be better to remove the flow control element and allow the tissue to function efficiently. The flow control element, however, is preferably not removed before the tissue has a sufficient chance to recover.

Figure 11:
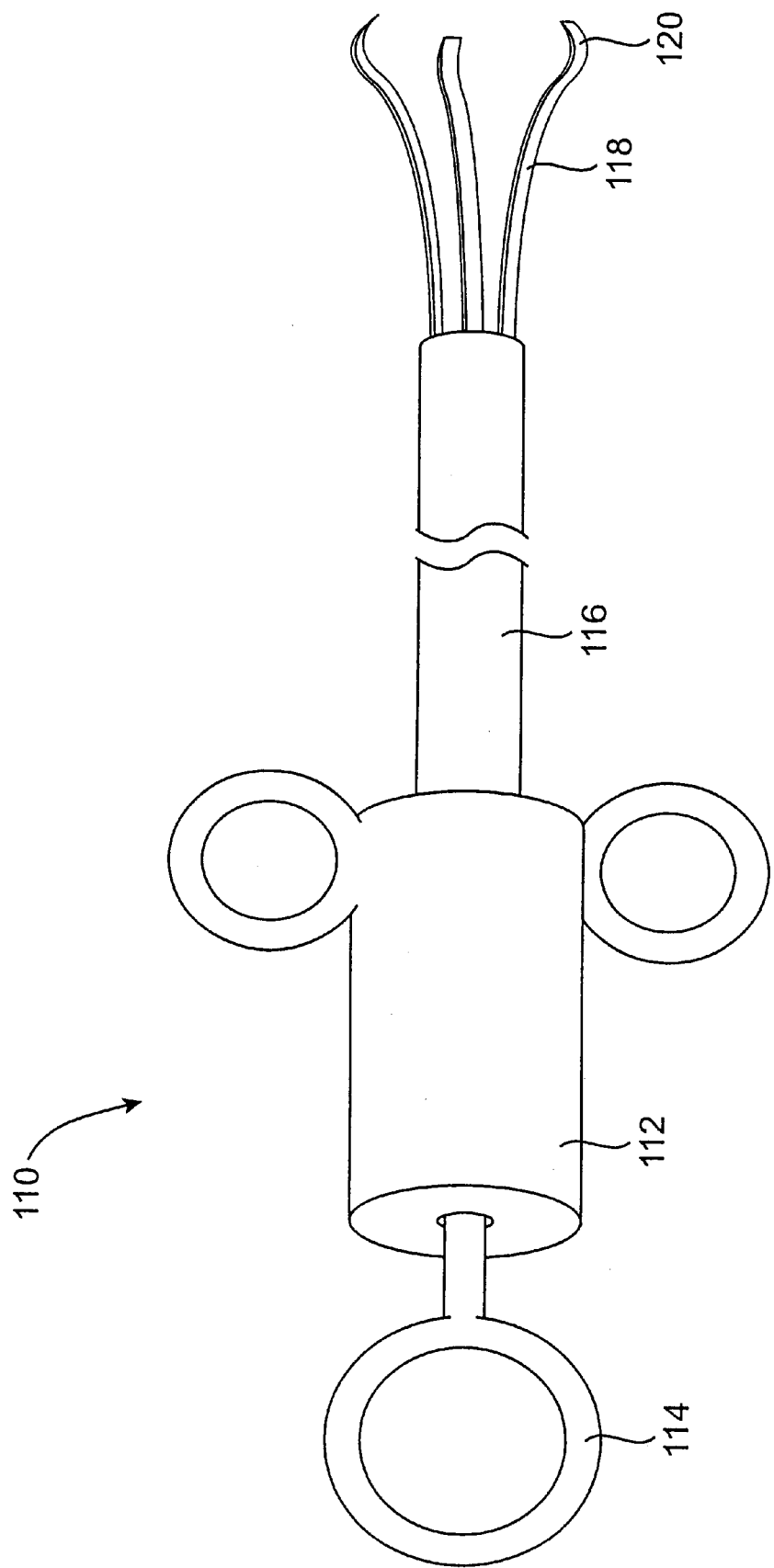
FIG. 11 is a perspective view of a removal device constructed according to another embodiment of the invention for removing a flow control element that has already been positioned in a hollow structure.

Accordingly, the invention also provides methods and devices for removing a flow control element from a hollow structure such as a bronchiole in a patient's body. FIG. 11 shows a device 110 comprising a handle 112, an actuator 114, a shaft 116 and one or more removal components 118. The components 118 preferably have tips 120 configured to grasp a flow control element in order to remove the element from surrounding tissue. The shaft 116 of the device 110 is passed into a patient's trachea (not shown) and is guided to the previously-deployed flow control element; for example, the shaft 116 may be introduced through the working channel of a bronchoscope in the same manner as the delivery device 20. The removal components 118 are preferably collapsed within shaft 116 while the shaft is guided to the site. The components 118 are then extended into contact with the wall of the bronchiole. The tips 120 are used to grasp and remove the flow control element from the bronchiole.

The flow control element of the invention is secured in position in the hollow structure, such as bronchiole 28, so as to remain in place during breathing. The exterior of the flow control element may be configured along all or part of its exterior to aid in fixing the element in place, for instance, as schematically indicated by reference numeral 48 in FIGS. 3 and 4. The fixation structure 48 may comprise adhesives, tissue growth-inducing substances, fasteners, staples, clips, suture, stents, balloons, Dacron® sleeves, sintered, etched, roughened, barbed or alternatively treated surfaces, etc.

Placement of a flow control element constructed according to the invention in a patient's pulmonary system achieves several benefits. With reference to the illustrated flow control element 22, when deployed in the bronchiole 28 as shown in FIGS. 1 and 2, the element allows exhalation but prevents inhalation. The flow control element 22 thus limits or prevents the inhalation of additional fluid into the diseased lung portion. This is beneficial because it prevents further enlargement of the hyper-expanded tissue, which in turn maintains more room in the pleural space for healthy lung tissue. The flow control element 22 also allows any air being naturally exhaled by the patient (as well as any liquid, if present) to exit the lung, thereby deflating or decompressing the tissue. The fluid is preferably permitted to flow unimpeded from the lung, but it may instead be metered or regulated in order to control deflation.

The flow control elements of the invention permit the diseased tissue to gradually deflate, either under the patient's own power or by applying relatively gentle suction for a given period of time. The suction may be applied intermittently or continuously by any suitable means. For example, a suction catheter could be passed through the flow control element in the bronchiole and into the distal tissue. The flow control element, for example, a valve member, would preferably seal around the catheter in order to prevent fluid moving distally past the valve.

The invention thus provides significant benefits as it permits fluid to be evacuated from the alveoli without collapsing the floppy walls of the narrow airways leading to them, problem with common lung diseases such as emphysema and COPD, as discussed above. Accordingly, the invention facilitates removal of more fluid from the diseased lung tissue than prior art approaches, the effect of which is more plural space available to the healthy lung tissue.

In addition, as noted above, using the invention to deflate the diseased lung tissue for a selected period of time, e.g., one month, may have beneficial results on the tissue by temporarily removing it from the respiratory circuit. The flow control element is preferably removed before the tissue begins to necrose, but is left in place a sufficiently long enough time that the tissue will not revert to its floppy, toneless state when the element is removed. Stated otherwise, it may be possible to use the invention as a means for repairing (rather than removing or obliterating) diseased lung tissue, either by controlling the fluid flow in the lung tissue or by controlling the fluid flow in combination with delivering one or more substances.

For example, some possible substances with which the invention may be used include gene therapy or angiogenesis factors for lung repair or re-establishment of tissue elasticity; growth factors; anti-growth or anti-angiogenesis factors (or substances to cause necrosis or apoptosis) to prevent re-establishment of air and blood flow; antibiotics to prevent infection; anti-inflammatory agents including steroids and cortisones; sclerosing drugs or materials to promote rapid healing, for example, to allow earlier removal of the flow control element; agents for absorbing remaining fluids; and sealing substances for enhancing isolation of the diseased tissue.

The portion of the lung being treated may be deflated over time through repeated natural inhalation and exhalation with the flow control element in place. Alternatively or additionally, a vacuum source may be coupled to the flow control element to draw fluid out of the diseased tissue in the manner discussed above. This deflation of the diseased portion may be performed alone or in conjunction with delivering biological substances. The pressures used to suction the lung portion are preferably low to avoid collapsing the walls of the narrow airways.

In the embodiments in which the flow control element comprises a valve, it may be formed of various materials and may be constructed in various manners. As an example, the valve may comprise an annulus or support ring formed of any suitable metal or synthetic material, with the valve member being formed of silicone, natural rubber, latex, polyurethane, polytetrafluoroethylene, a thermoplastic elastomer, tissue, etc. The valve member may be integral with the support ring or it may be a separate member attached thereto by suitable means, e.g., suture, adhesives, mechanical fasteners, etc. If the flow control element comprises a stent with a valve, prior art attachment methods may be used. For example, see U.S. Pat. No. 5,954,766, the content of which is incorporated herein by reference.

The specific characteristics of the flow control element may be varied depending on the particular application. It may be desirable to provide multiple flow control elements with valve members that require different exhale pressures to open, for example, in order to allow treatment of patients who generate different exhalation pressures. The different flow control elements could be provided in a kit and be distinguished from each other based on required opening force, size, material, etc. The kit could include a color or other coding system to indicate these factors.

The flow control elements of the invention are preferably constructed so as to require a relatively low opening force in order to allow fluid flow in the first direction. Emphysema patients typically exhale a small quantity of low-pressure fluid. The invention preferably allows any such fluid to escape via the flow control element in the hollow structure. As such, the flow control element is designed to open and allow flow in the first direction in response to any positive pressure generated by the patient. Put another way, as long as some pressure differential exists between the distal lung tissue and the proximal portion of the bronchiole, the flow control element will open to allow fluid to escape the tissue. It will nonetheless be recognized that the particular force required to open the flow control element may be varied depending on exhalation pressures associated with the intended patient population.

It will be appreciated that features of the various preferred embodiments of the invention may be used independently or in conjunction with one another, while the illustrated methods and devices may be modified or combined in whole or in part. The inventive devices may include removable or detachable components, and may comprise disposable or reusable components, or a combination of disposable and reusable components. Likewise, it will be understood that the invention may be practiced with one or more of the steps specifically illustrated and described herein modified or omitted.

It should also be recognized that the invention is not limited to treating lung diseases as is shown in the Figures, although that is a preferred application. The invention may be used in any pulmonary or non-pulmonary procedure in which it is desirable to allow fluid flow in a first direction and control fluid flow in a second, different direction within a hollow structure. Finally, it will be understood that although a minimally invasive, endobronchial approach is shown in the Figures, other approaches may used, for example, an open surgical procedure using a median sternotomy, a minimally invasive procedure using a mini thoracotomy, or a still less invasive procedure using one or more ports or openings in the thorax, etc.

The preferred embodiments of the invention are described above in detail for the purpose of setting forth a complete disclosure and for sake of explanation and clarity. It will be readily understood that the scope of the invention defined by the appended claims will encompass numerous changes and modifications.

What is claimed is:

1. A system for use in a lung of a patient comprising:
   a scope adapted for viewing a lung passageway in the lung, the scope having a shaft positionable in the patient's trachea and a working channel in the shaft;
   a delivery device movably positionable in the working channel;
   a flow control element releasably coupled to the delivery device and adapted for implanting in the lung passageway to restrict fluid flow in at least an inspiration direction therethrough, wherein the delivery device comprises a support shaft configured for coupling to the flow control element and a sheath slidably disposed over the support shaft and configured to cover at least a portion of the flow control element, the sheath having an opening at a distal end thereof for insertion and removal of the flow control element; and an actuator associated with the delivery device for moving the sheath relative to the shaft to release the flow control element through the distal opening in the sheath.

2. The system of claim 1, wherein the flow control element is movable between a collapsed configuration for positioning into the lung passageway and an expanded configuration for implanting in the lung passageway.

3. The system of claim 2, wherein the delivery device is adapted to hold the flow control element in the collapsed configuration.

4. The system of claim 2, wherein the flow control element comprises a stent movable between a collapsed configuration and an expanded configuration.

5. The system of claim 4, wherein the stent comprises a resilient material so as to self-expand from the collapsed configuration to the expanded configuration.

6. The system of claim 1, wherein the flow control element comprises a fixation structure thereon to aid in fixing the flow control element in place in the lung passageway.

7. The system of claim 6, wherein the fixation structure comprises a plurality of barbs for engaging a wall of the lung passageway.

8. The system of claim 1, wherein moving the actuator decouples the flow control element from the delivery device.

9. The system of claim 1, wherein the flow control element comprises a valve which restricts fluid flow in the inspiration direction and allows fluid flow in the expiration direction.

10. The system of claim 1, wherein the bronchoscope has a distal end, the delivery device being movable distally of the distal end so that the flow control element is visible through the scope.

11. The system of claim 1, wherein the flow control element is movably positionable within the working channel.

12. The system of claim 1, wherein the scope has a port at a proximal end thereof in communication with the working channel, the delivery device being positionable through the port.

13. A system for treating a lung of a patient through a working channel of a bronchoscope positioned in the patient's trachea, the system comprising:
 a delivery device movably positionable in the working channel;
 a flow control element releasably coupled to the delivery device and adapted for implanting in the lung passageway to restrict fluid flow in at least an inspiration direction therethrough, wherein the delivery device comprises a support shaft configured for coupling to the flow control element and a sheath slidably disposed over the support shaft and configured to cover at least a portion of the flow control element, the sheath having an opening at a distal end thereof for insertion and removal of the flow control element; and
 an actuator associated with the delivery device for moving the sheath relative to the shaft to release the flow control element through the distal opening in the sheath.

14. The system of claim 13, wherein the flow control element is movable a collapsed configuration for positioning into the lung passageway and an expanded configuration for implanting in the lung passageway.

15. The system of claim 14, wherein the delivery device is adapted to hold the flow control element in the collapsed configuration.

16. The system of claim 14, wherein the flow control element comprises a stent movable between a collapsed configuration and an expanded configuration.

17. The system of claim 16, wherein the stent comprises a resilient material so as to self-expand from the collapsed configuration to the expanded configuration.

18. The system of claim 13, wherein the flow control element comprises a fixation structure thereon to aid in fixing the flow control element in place in the lung passageway.

19. The system of claim 18, wherein the fixation structure comprises a plurality of barbs for engaging a wall of the lung passageway.

20. The system of claim 13, wherein moving the actuator decouples the flow control element from the delivery device.

21. The system of claim 13, wherein the flow control element comprises a valve which restricts fluid flow in the inspiration direction and allows fluid flow in the expiration direction.

22. The system of claim 13, wherein the bronchoscope has a distal end, the delivery device being movable distally of the distal end so that the flow control element is visible through the scope.

23. The system of claim 13, wherein the flow control element is movably positionable within the working channel.

24. The system of claim 13, wherein the scope has a port at a proximal end thereof in communication with the working channel, the delivery device being positionable through the port.

25. A method for treating a patient's lung, the method comprising steps of:
 providing a flow control element which restricts fluid flow in at least a first direction, the flow control element being releasably coupled to a delivery device;
 inserting a bronchial access device in a bronchial passageway of a patient's lung, the bronchial access device having a first channel and a second channel;
 positioning the delivery device in the second channel; and
 deploying the flow control element at the treatment site;
 wherein the inserting step comprises positioning a distal end of the bronchial access device in a first bronchial passageway and the deploying step comprises placing the flow control element in a second bronchial passageway branching from the first bronchial passageway.

26. The method of claim 25, further comprising visualizing a treatment site in the patient's lung through the first channel.

27. The method of claim 25, wherein the bronchial access device comprises a bronchoscope.

28. The method of claim 25, wherein the flow control element restricts flow in only the first direction.

29. The method of claim 28, wherein the flow control element comprises a valve.

30. The method of claim 29, wherein the valve is selected from the group consisting of duckbill, flapper, tricuspid, ball and needle valves.

31. The method of claim 25, wherein at least a portion of the flow control element has a first diameter before the deploying step and a second diameter when deployed at the treatment site, the first diameter being less than the second diameter.

32. The method of claim 31, wherein the flow control element comprises a stent, and wherein during the deploying step the stent expands from the first diameter to the second diameter.

33. The method of claim 25, wherein the flow control element is advanced through the second channel during the positioning step.

34. The method of claim 25, wherein the delivery device is positioned in the second channel after the inserting step.

35. The method of claim 25, further comprising visualizing the flow control element through the first channel during the step of deploying.

36. The method of claim 25, wherein the bronchial access device includes a camera.

37. The method of claim 25, wherein the visualizing step comprises transmitting light through a lens.

38. The method of claim 25, further comprising, prior to carrying out the deploying step, determining the approximate size of the treatment site, and selecting an appropriately sized flow control element based at least in part on the determined size of the treatment site.

39. The method of claim 38, wherein the determining step is carried out using a measuring device.

40. The method of claim 25, further comprising the step of applying suction to at least part of the lung located distally of the flow control element.

41. A method for treating a patient's lung, the method comprising steps of:

providing a flow control element which restricts fluid flow in at least a first direction, the flow control element being releasably coupled to a delivery device, wherein the delivery device has a sheath, the sheath having an opening at a distal end thereof;

inserting a bronchial access device in a bronchial passageway of a patient's lung, the bronchial access device having a first channel and a second channel;

positioning the delivery device in the second channel; and deploying the flow control element at the treatment site, the deploying step comprising moving the sheath relative to the flow control element to release the flow control element through the distal opening in the sheath.

42. The method of claim 41, further comprising visualizing the flow control element through the first channel during the step of deploying.

43. The method of claim 41, wherein the bronchial access device includes a camera.

44. The method of claim 41, wherein the visualizing step comprises transmitting light through a lens.

45. The method of claim 41, wherein the inserting step comprises positioning a distal end of the bronchial access device in a first bronchial passageway and the deploying step comprises placing the flow control element at a second bronchial passageway branching from the first bronchial passageway.

46. The method of claim 41, further comprising, prior to carrying out the deploying step, determining the approximate size of the treatment site, and selecting an appropriately sized flow control element based at least in part on the determined size of the treatment site.

47. The method of claim 41, further comprising the step of applying suction to at least part of the lung located distally of the flow control element.

48. The method of claim 41, wherein the bronchial access device comprises a bronchoscope.

* * * * *

UNITED STATES PATENT AND TRADEMARK OFFICE
CERTIFICATE OF CORRECTION

PATENT NO.         : 6,840,243 B2                                        Page 1 of 1
APPLICATION NO.    : 10/419508
DATED              : January 11, 2005
INVENTOR(S)        : Deem et al.

It is certified that error appears in the above-identified patent and that said Letters Patent is hereby corrected as shown below:

IN THE CLAIMS:
Claim 14 should read as follows:
    14.    The system of claim 13, wherein the flow control element is movable between a collapsed configuration for positioning into the lung passageway and an expanded configuration for implanting in the lung passageway.

Signed and Sealed this

Third Day of October, 2006

JON W. DUDAS
*Director of the United States Patent and Trademark Office*